(12) United States Patent
Qiu

(10) Patent No.: US 10,617,153 B2
(45) Date of Patent: Apr. 14, 2020

(54) ELECTRONIC CIGARETTE AND ATOMIZER FOR SAME

(71) Applicant: CHANGZHOU PATENT ELECTRONIC TECHNOLOGY CO., LTD., Changzhou (CN)

(72) Inventor: Weihua Qiu, Changzhou (CN)

(73) Assignee: CHANGZHOU PATENT ELECTRONIC TECHNOLOGY CO., LTD., Jiangsu (CN)

( * ) Notice: Subject to any disclaimer, the term of this patent is extended or adjusted under 35 U.S.C. 154(b) by 134 days.

(21) Appl. No.: 15/826,432

(22) Filed: Nov. 29, 2017

(65) Prior Publication Data

US 2018/0160736 A1 Jun. 14, 2018

(30) Foreign Application Priority Data

Dec. 14, 2016 (CN) .................... 2016 2 1375893 U

(51) Int. Cl.
*A24F 47/00* (2020.01)
*A61M 11/04* (2006.01)
*A61M 15/06* (2006.01)

(52) U.S. Cl.
CPC .......... *A24F 47/008* (2013.01); *A61M 15/06* (2013.01); *A61M 11/042* (2014.02); *A61M 2205/8206* (2013.01)

(58) Field of Classification Search
CPC ....... A24F 47/00; A24F 47/008; A61M 11/04; A61M 11/042; A61M 15/06
See application file for complete search history.

(56) References Cited

U.S. PATENT DOCUMENTS

| | | | |
|---|---|---|---|
| 9,132,248 B2* | 9/2015 | Qiu | A61M 11/041 |
| 2015/0157055 A1* | 6/2015 | Lord | A24F 47/008 |
| | | | 131/329 |
| 2015/0272217 A1* | 10/2015 | Chen | A24F 47/008 |
| | | | 131/329 |
| 2015/0305406 A1* | 10/2015 | Li | A24F 47/008 |
| | | | 131/329 |
| 2016/0128385 A1* | 5/2016 | Lin | A24F 47/008 |
| | | | 131/328 |
| 2017/0325504 A1* | 11/2017 | Liu | A24F 47/00 |

* cited by examiner

*Primary Examiner* — Ryan A Reis
(74) *Attorney, Agent, or Firm* — J.C. Patents

(57) ABSTRACT

Embodiments of the present disclosure provide an atomizer including an atomizing assembly and a liquid storage tube for supplying smoke liquid to the atomizing assembly; the liquid storage tube is provided with a liquid storage cavity and a liquid outlet in communication with the liquid storage cavity; the atomizing assembly includes a base, the base is provided with an accommodating cavity and at least one atomizing cavity; the accommodating cavity is correspondingly disposed with respect to the liquid outlet, each atomizing cavity is in communication with the accommodating cavity; the atomizing assembly further includes a first liquid guiding element disposed in the accommodating cavity, and a heating element and a second liquid guiding element disposed in the atomizing cavity, wherein the first liquid guiding element is in communication with the second liquid guiding element.

12 Claims, 3 Drawing Sheets

ELECTRONIC CIGARETTE AND ATOMIZER FOR SAME

CROSS-REFERENCE TO RELATED APPLICATIONS

This application claims priority to Chinese Patent Application No. 201621375893.9, filed on Dec. 14, 2016, entitled "An electronic cigarette and an atomizer for same", which is incorporated herein by reference in its entirety.

TECHNICAL FIELD

The present disclosure relates to the technical field of smoking simulating, and in particular, to an electronic cigarette and an atomizer for same.

BACKGROUND

After being absorbed by a liquid guiding element on an atomizer of an existing electronic cigarette, the smoke liquid is atomized into smoke via the heating of a heating element for users to use. However, in the structure of the conventional electronic cigarette, there is usually merely one liquid guiding element, and the liquid guiding element, which is wound by the heating element, directly absorbs the smoke liquid in a liquid storage tube. When the electronic cigarette is left unused for a long time, liquid leakages may be caused due to a supersaturation of the smoke liquid absorbed by the liquid guiding element, thereby not only polluting the electronic cigarette but also reducing user experiences.

SUMMARY

Based on this, it is necessary to provide an electronic cigarette and an atomizer for same, so as to reduce the leakage caused by the electronic cigarette being placed for a long period of time.

The technical scheme to be used in solving the technical problem of the present disclosure is: an atomizer, where the atomizer includes an atomizing assembly and a liquid storage tube for supplying smoke liquid to the atomizing assembly; the liquid storage tube is provided with a liquid storage cavity and a liquid outlet in communication with the liquid storage cavity; the atomizing assembly includes a base, the base is provided with an accommodating cavity and at least one atomizing cavity; the accommodating cavity is correspondingly disposed with respect to the liquid outlet, each atomizing cavity is in communication with the accommodating cavity; the atomizing assembly further includes a first liquid guiding element disposed in the accommodating cavity, and a heating element and a second liquid guiding element disposed in the atomizing cavity, wherein the first liquid guiding element is in liquid communication with the second liquid guiding element.

Further, an upper end surface of the base is depressed downwardly to form the accommodating cavity and the atomizing cavity; a liquid guiding groove is provided on a bottom of the accommodating cavity, such that the accommodating cavity is in intercommunication with each atomizing cavity.

Further, the atomizer includes a shell sleeved on the liquid storage tube, where the base is fixedly accommodated at a lower end of the shell, at least one first air inlet hole is defined on a side wall of the shell.

Further, each atomizing cavity is provided with a fixing bracket, the heating element and the second liquid guiding element are fixedly mounted on the fixing bracket after being wound with each other.

Further, one air outlet groove corresponding to one atomizing cavity is defined on an outer side wall of the liquid storage tube, the air outlet groove is in communication with the corresponding atomizing cavity; one second air inlet hole corresponding to one atomizing cavity is defined on a side wall of the base, the first air inlet hole is in communication with the second air inlet hole.

Further, a clamping groove is disposed in a concave way on an inner wall of the shell along a circumferential direction of the shell, the base is provided with a buckle corresponding to the clamping groove, the base is fixedly connected to the shell via a fitting between the clamping groove and the buckle.

Further, the atomizer further includes an upper cover disposed on an upper end of the shell, where an air outlet hole is defined on the upper cover, and the air outlet hole is in communication with the air outlet groove.

Further, an edge of a lower end of the upper cover extends downwardly to form a coupling ring, and the coupling ring is fixedly accommodated at the upper end of the shell.

Further, a liquid inlet is disposed on an upper end of the liquid storage tube, and a seal is mounted on the liquid inlet.

An electronic cigarette, the electronic cigarette includes: an atomizer according to any one hereinabove, the electronic cigarette further includes a battery assembly electrically connected to the atomizer.

The present disclosure has following advantages: in the atomizer or the electronic cigarette of the present disclosure, the smoke liquid is absorbed by the first liquid guiding element and then absorbed by the second liquid guiding element, the smoke liquid on the second liquid guiding element is atomized into smoke under the heating of the heating element. Compared with the conventional structure, it is ensured that the smoke liquid is not directly absorbed by the second liquid guiding element, thus avoiding a possible leakage phenomenon due to a long period of placement.

BRIEF DESCRIPTION OF DRAWINGS

Further descriptions to the present disclosure are made with reference to accompanying drawings and embodiments in the following.

Figure 1:
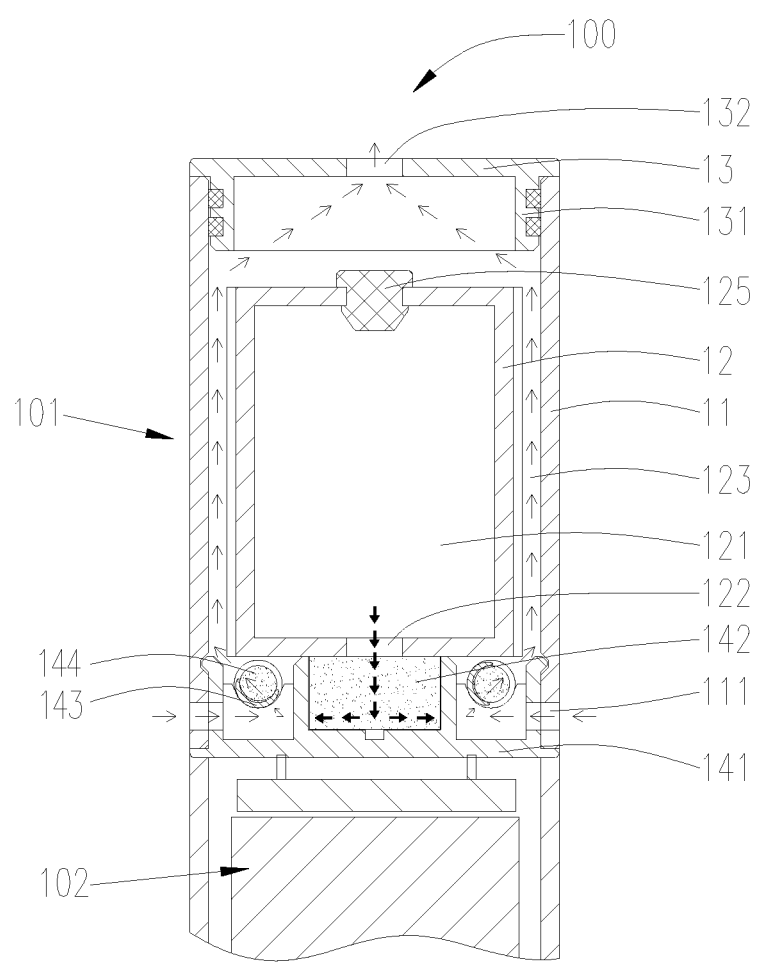
FIG. 1 is a structural view of an electronic cigarette according to the present disclosure.

Names of components in the drawings and numbers for same are respectively illustrated as follows:

| Electronic cigarette 100 | Atomizer 101 | Battery assembly 102 |
|---|---|---|
| Shell 11 | Liquid storage tube 12 | Upper cover 13 |
| Atomizing assembly 14 | First air inlet hole 111 | Liquid storage cavity 121 |
| Liquid outlet 122 | Air outlet groove 123 | Liquid inlet 124 |
| Seal 125 | Coupling ring 131 | Air outlethole 132 |
| Base 141 | First liquid guiding element 142 | Heating element 143 |
| Buckle 1411 | Accommodating cavity 1412 | Atomizing cavity 1413 |

| | | |
|---|---|---|
| Liquid guiding groove 1414 | Second air inlet hole 1415 | Fixing bracket 1416 |
| Second liquid guiding element 144 | Clamping groove 112 | |

DESCRIPTION OF EMBODIMENTS

The present disclosure will now be described in detail with reference to the accompanying drawings. These drawings are simplified schematic views, and the basic structure of the present disclosure will merely be described in a schematic manner. Therefore, they merely show configurations related to the present disclosure.

Figure 4:
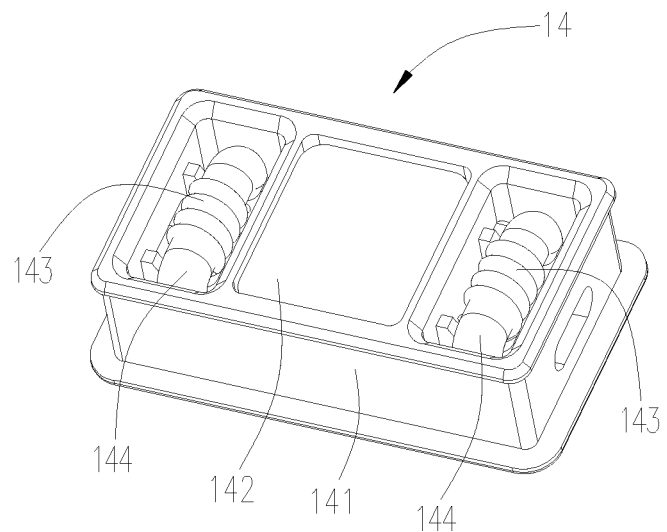
FIG. 4 is a structural view of an atomizing assembly of the electronic cigarette shown in FIG. 1.

As shown in FIGS. 1 and 4, the present disclosure provides an electronic cigarette 100, the electronic cigarette 100 includes an atomizer 101 and a battery assembly 102 electrically connected thereof. The atomizer 101 includes a shell 11, a liquid storage tube 12 fixedly accommodated to the shell 11, an upper cover 13 disposed at an upper end of the shell 11, and an atomizing assembly 14 disposed below the liquid storage tube 12.

Figure 2:
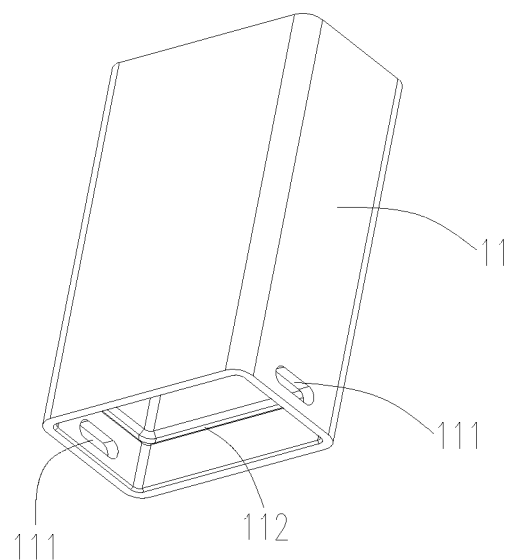
FIG. 2 is a structural view of a shell of the electronic cigarette shown in FIG. 1.

As shown in FIG. 2, the shell 11 exhibits a hollow columnar structure with apertures on both ends. Two first air inlet holes 111 are oppositely defined on side walls of a lower end of the shell 11. A annular clamping groove 112 is disposed in a concave way on an inner wall of the shell 11 along a circumferential direction of the shell 11. The clamping groove 112 is disposed above the first air inlet hole 111.

Figure 3:
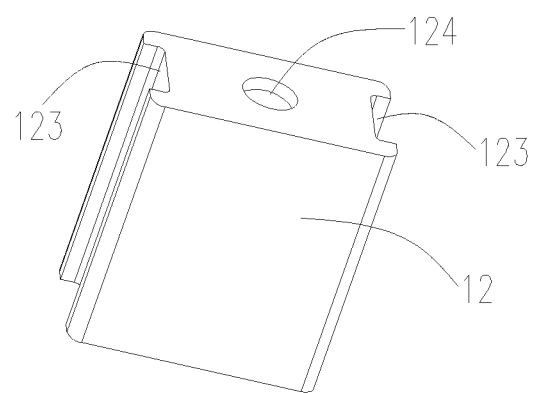
FIG. 3 is a structural view of a liquid storage tube of the electronic cigarette shown in FIG. 1.

As shown in FIG. 3, the liquid storage tube 12 substantially exhibits a hollow columnar structure, so an internal space of the liquid storage tube 12 forms a liquid storage cavity 121 for storing smoke liquid. A liquid outlet 122 in communication with the liquid storage cavity 121 is defined on a lower end of the liquid storage tube 12. On an outer side wall of the liquid storage tube 12, a pair of air outlet grooves 123 is oppositely defined in the direction along a central axis of the liquid storage tube 12.

In one of the implementation manners, a liquid inlet 124 for communicating with the liquid storage cavity 121 is defined on an upper end of the liquid storage tube 12. Therefore, a user can add the smoke liquid to the liquid storage cavity 121 through the liquid inlet 124. In order to prevent the smoke liquid in the liquid storage cavity 121 from leaking out of the liquid inlet 124, after the filling of the smoke liquid is completed, the liquid inlet 124 may be sealed by a seal 125. In the present implementation manner, a silicone plug is employed as the seal 125 to improve a sealing performance.

The upper cover 13 substantially exhibits a plate-like structure. An edge of a lower end of the upper cover 13 extends downwardly to form a coupling ring 131. The coupling ring 131 is fixedly accommodated at an upper end of the shell 11. In order to improve the airtightness, a seal (not shown) is provided between the coupling ring 131 and the shell 11. The seal may be a silicone ring or the like. It should be appreciated that in other implementation manners which are not shown herein, the coupling ring 131 may also be fixedly connected to the shell 11 in a clamped connecting manner or a threaded connecting manner, etc.

In one of the implementation manners, an air outlet hole 132 is defined on the upper cover 13. When the liquid storage tube 12 and the upper cover 13 are mounted in place, the air outlet hole 132 can communicate with the air outlet groove 123 of the liquid storage tube 12. When being used, the user may smoke through the air outlet hole 132. It is also possible to mount a communicating element, such as a cigarette holder on the air outlet hole 132, so that the user may hold the cigarette holder for smoking.

Figure 5:
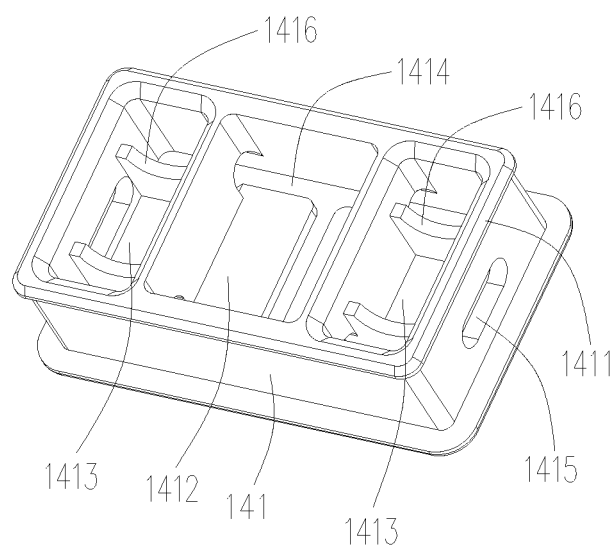
FIG. 5 is a structural view of a base of the atomizing assembly shown in FIG. 4.

As shown in FIGS. 4 and 5, the atomizing assembly 14 includes a base 141, a first liquid guiding element 142, a heating element 143, and a second liquid guiding element 144 which are mounted, respectively, on the base 141.

The base 141 substantially exhibits a box-like structure, and the base 141 is fixedly accommodated at a lower end of the shell 11. An annular buckle 1411 is disposed in a convex way on an edge of an upper end of the base 141 corresponding to the clamping groove 112 of the shell 11. The base 141 is fixedly connected to the shell 11 via a fitting between the clamping groove 112 and the buckle 1411, and the upper end of the base 141 is butted against the lower end of the liquid storage tube 12.

A middle portion of an upper end surface of the base 141 is depressed downwardly to form the accommodating cavity 1412, and the accommodating cavity 1412 is in communication with the liquid outlet 122 of the liquid storage tube 12. The upper surface of the base 141 on opposite sides of the accommodating cavity 1412 is depressed downwardly to form two atomizing cavities 1413, and one atomizing cavity 1413 is in communication with one air outlet groove 123 of the liquid storage tube 12. The first liquid guiding element 142 is mounted in the accommodating cavity 1412, and can suck the smoke liquid through the liquid outlet 122. One heating element 143 and one second liquid guiding element 144 are mounted in one atomizing cavity 1413. A liquid guiding groove 1414 is provided on a bottom of the accommodating cavity 1412 for being in communication with each atomizing cavity 1413, so that the smoke liquid in the accommodating cavity 1412 can enter into the atomizing cavities 1413 through the liquid guiding groove 1414.

In one of the implementation manners, two second air inlet holes 1415 corresponding to the first air inlet holes 111 are oppositely defined on the side wall of the base 141, one second air inlet hole 1415 is in communication with its adjacent atomizing cavity 1413. When the base 141 is mounted to the lower end of the shell 11, the first air inlet hole 111 is in corresponding communication with the second air inlet hole 1415.

In one of the implementation manners, a fixing bracket 1416 is provided in each atomizing cavity 1413.

The heating element 143 and the second liquid guiding element 144 are fixedly mounted on the fixing bracket 1416 after being wound with each other. In the present implementation manner, the heating element 143 is a heating wire, the second liquid guiding element 144 is cotton, the heating element 143 is wound on the second liquid guiding element 144 or the second liquid guiding element 144 is wound on the heating element 143. The second liquid guiding element 144 is capable of absorbing the smoke liquid in the atomizing cavity 1413, and the heating element 143 is electrically connected to the battery assembly 102 for atomizing the smoke liquid.

Specifically, the battery assembly 102 is fixedly connected to the lower end of the shell 11. It should be understood that the battery assembly 102 and the shell 11 may be fixedly connected in a threaded connecting manner, a clamped connecting manner or in a inserted connecting manner.

The operation of the atomizer 101 of the present disclosure will be described below with reference to the drawings.

As shown in FIGS. 1 and 4, the smoke liquid in the liquid storage cavity 121 is absorbed by the first liquid guiding element 142 in the accommodating cavity 1412 through the liquid outlet 122 at the lower end. When the first liquid guiding element 142 becomes saturated, the redundant smoke is then stored in the accommodating cavity 1412. The smoke liquid is introduced into the atomizing cavities 1413 locating on both sides of the accommodating cavity 1412 via the liquid guiding groove 1414, then absorbed by the second liquid guiding element 144, and becomes smoke after being heated by the heating element 143. The direction of thicker arrows in FIG. 1 represents the flow direction of the smoke liquid.

When the user sucks, air from outside enters into the atomizing cavity 1413 after passing through the first air inlet hole 111 of the shell 11 and the second air inlet hole 1415 of the base 141 and is mixed with smoke. The mixed gas passes through the air outlet grooves 123 on both sides of the liquid storage tube 12 and successively the air outlet hole 132 of the upper cover 13, and finally reaches the user's mouth. The direction of thinner arrows in FIG. 1 represents the direction of the airflow.

It should be understood that the shell 11 may also be provided with a control structure (not shown). The control structure may be a button or a knob, by pressing or rotating the control structure, it is possible to change a parallel or series relationship between the two heating elements 143. The working power of the heating element 143 may vary along with different connecting manners in series or parallel, thus resulting in different atomizing effects, thereby adapting needs from different users. Alternatively, the control structure can control each of the heating elements 143 to operate alone, for example, during the using process, one of the heating elements 143 is in a dry-fire condition, then the heating operation of this heating element 143 may be stopped by the control structure while the other heating element 143 is still working normally, thus avoiding the problem of frequent replacements of the atomizing assembly 14 by the user.

It should be understood that there is one or more than two atomizing cavities 1413 on the atomizing assembly 14, where one heating element 143 and one second liquid guiding element 144 are provided in one the atomizing cavity 1413 at the same time. Specifically, there is only one atomizing cavity 1413, the atomizing cavity 1413 may be disposed on one side of the accommodating cavity 1412. There are more than two atomizing cavities 1413, the atomizing cavities 1413 are all disposed around the accommodating cavity 1412. At this time, the number of the air outlet grooves 123 on the liquid storage tube 12 is as same as that of the atomizing cavities 1413, and one air outlet groove 123 is in communication with one corresponding atomizing cavity 1413. In one of the implementation manners, the number of the first air inlet holes 111 defined on the shell 11 and the number of the second air inlet holes 1415 defined on the base 141 are both as same as that of the atomizing cavities 1413, and are both in communication with corresponding atomizing cavities 1413. It should be understood that the greater the number of second liquid guiding element 144 is, the longer the time to be placed without leakage becomes.

The atomizer 101 provided according to the present disclosure, a first liquid guiding element 142 and a second liquid guiding element 144 are respectively disposed on the atomizing assembly 14, the smoke liquid is absorbed by first liquid guiding element 142 and then absorbed by the second liquid guiding element 144, and the smoke liquid on the second liquid guiding element 144 is atomized into smoke under the heating of the heating element 143. Compared with the traditional structure, the present disclosure ensures that smoke liquid is not directly absorbed by the second liquid guiding element 144, thus avoiding a possible leakage phenomenon due to a long period of placement.

The electronic cigarette 100 provided according to the present disclosure may achieve the same technical effect as the atomizer 101 because the electronic cigarette 100 includes all the technical features of the above-described atomizer 101.

In view of the above-described ideal embodiments according to the present disclosure, it is possible for the related staff to make various changes and modifications without departing from the scope of the present disclosure. The technical scope of the present disclosure is not limited to the contents of the specification, and must be determined according to the scope of the claims.

What is claimed is:

1. An atomizer, wherein the atomizer comprises: an atomizing assembly and a liquid storage tube for supplying smoke liquid to the atomizing assembly; the liquid storage tube is provided with a liquid storage cavity and a liquid outlet in communication with the liquid storage cavity;

the atomizing assembly comprises a base, the base is provided with an accommodating cavity and at least one atomizing cavity; the accommodating cavity is correspondingly disposed with respect to the liquid outlet, each atomizing cavity is in communication with the accommodating cavity;

the atomizing assembly further comprises a first liquid guiding element disposed in the accommodating cavity, and a heating element and a second liquid guiding element disposed in the atomizing cavity, wherein the first liquid guiding element is in liquid communication with the second liquid guiding element;

wherein the atomizer further comprises:

a shell sleeved on the liquid storage tube, wherein the base is fixedly accommodated at a lower end of the shell, at least one first air inlet hole is defined on a side wall of the shell;

wherein one air outlet groove corresponding to one atomizing cavity is defined on an outer side wall of the liquid storage tube, the air outlet groove is in communication with the corresponding atomizing cavity; one second air inlet hole corresponding to one atomizing cavity is defined on a side wall of the base, the first air inlet hole is in communication with the second air inlet hole;

wherein a clamping groove is disposed in a concave way on an inner wall of the shell along a circumferential direction of the shell, the base is provided with a buckle corresponding to the clamping groove, the base is fixedly connected to the shell via a fitting between the clamping groove and the buckle.

2. The atomizer according to claim 1, wherein an upper end surface of the base is depressed downwardly to form the accommodating cavity and the atomizing cavity; a liquid guiding groove is provided on a bottom of the accommodating cavity, such that the accommodating cavity is in intercommunication with each atomizing cavity.

3. The atomizer according to claim 1, wherein each atomizing cavity is provided with a fixing bracket, wherein the heating element and the second liquid guiding element are fixedly mounted on the fixing bracket after being wound with each other.

4. The atomizer according to claim 1, wherein the atomizer further comprises:

an upper cover disposed on an upper end of the shell, wherein an air outlet hole is defined on the upper cover, and the air outlet hole is in communication with the air outlet groove.

5. The atomizer according to claim 4, wherein an edge of a lower end of the upper cover extends downwardly to form a coupling ring, and the coupling ring is fixedly accommodated at the upper end of the shell.

6. The atomizer according to claim 1, wherein a liquid inlet is disposed on an upper end of the liquid storage tube, and a seal is mounted on the liquid inlet.

7. An electronic cigarette, wherein the electronic cigarette comprises:
   an atomizer according to claim 1, wherein the electronic cigarette further comprises a battery assembly electrically connected to the atomizer;
   wherein the atomizer further comprises:
   a shell sleeved on the liquid storage tube, wherein the base is fixedly accommodated at a lower end of the shell, at least one first air inlet hole is defined on a side wall of the shell;
   wherein one air outlet groove corresponding to one atomizing cavity is defined on an outer side wall of the liquid storage tube, the air outlet groove is in communication with the corresponding atomizing cavity; one second air inlet hole corresponding to one atomizing cavity is defined on a side wall of the base, the first air inlet hole is in communication with the second air inlet hole;
   wherein a clamping groove is disposed in a concave way on an inner wall of the shell along a circumferential direction of the shell, the base is provided with a buckle corresponding to the clamping groove, the base is fixedly connected to the shell via a fitting between the clamping groove and the buckle.

8. The electronic cigarette according to claim 7, wherein an upper end surface of the base is depressed downwardly to form the accommodating cavity and the atomizing cavity; a liquid guiding groove is provided on a bottom of the accommodating cavity, such that the accommodating cavity is in intercommunication with each atomizing cavity.

9. The electronic cigarette according to claim 7, wherein each atomizing cavity is provided with a fixing bracket, wherein the heating element and the second liquid guiding element are fixedly mounted on the fixing bracket after being wound with each other.

10. The electronic cigarette according to claim 7, wherein the atomizer further comprises:
    an upper cover disposed on an upper end of the shell, wherein an air outlet hole is defined on the upper cover, and the air outlet hole is in communication with the air outlet groove.

11. The electronic cigarette according to claim 10, wherein an edge of a lower end of the upper cover extends downwardly to form a coupling ring, and the coupling ring is fixedly accommodated at the upper end of the shell.

12. The electronic cigarette according to claim 7, wherein a liquid inlet is disposed on an upper end of the liquid storage tube, and a seal is mounted on the liquid inlet.

* * * * *